United States Patent [19]

Plischka

[11] Patent Number: 4,668,191
[45] Date of Patent: May 26, 1987

[54] JAW IMPLANT FOR RECEIVING A REPLACEMENT-TOOTH HOLDER

[75] Inventor: Gerhard Plischka, Graz, Austria

[73] Assignee: Feldmuehle Aktiengesellschaft, Duesseldorf, Fed. Rep. of Germany

[21] Appl. No.: 738,692

[22] Filed: May 28, 1985

[30] Foreign Application Priority Data

Jun. 6, 1984 [DE] Fed. Rep. of Germany ....... 3421056

[51] Int. Cl.⁴ .................... A61C 1/24; A61C 13/00; A61C 13/30
[52] U.S. Cl. ................................................. 433/174
[58] Field of Search ................ 433/173, 174, 175, 176

[56] References Cited

U.S. PATENT DOCUMENTS

| | | | |
|---|---|---|---|
| 3,514,858 | 6/1970 | Silverman | 433/174 |
| 3,579,831 | 5/1971 | Stevens | 433/174 |
| 4,223,412 | 9/1980 | Aoyagi et al. | 433/201.1 |
| 4,468,200 | 8/1984 | Munch | 433/174 |

FOREIGN PATENT DOCUMENTS

| | | | |
|---|---|---|---|
| 92209A3 | 4/1983 | European Pat. Off. | 433/173 |
| 2540077 | 9/1975 | Fed. Rep. of Germany | 433/174 |
| 2615116 | 4/1976 | Fed. Rep. of Germany | 433/174 |
| 2628443 | 6/1976 | Fed. Rep. of Germany | 433/174 |
| 3043336 | 11/1979 | Fed. Rep. of Germany | 433/174 |
| 3315329 | 11/1983 | Fed. Rep. of Germany | 433/173 |
| WO83/00616 | 3/1983 | PCT Int'l Appl. | 433/173 |
| 2063680 | 11/1979 | United Kingdom | 433/174 |

OTHER PUBLICATIONS

"Die Quintessenz" 1984 Heft 4, Seiten 665–669.
"Die Quintessenz" 1983 Heft 11, Seiten 2109–2114.

Primary Examiner—Robert Peshock
Attorney, Agent, or Firm—Felfe & Lynch

[57] ABSTRACT

A jaw implant having a bore to accommodate a replacement tooth holder, which has a screw head and a lower portion provided with a screw thread. The screw head is configured and proportioned such that the portion provided for embedment into the cortical bone tissue is of cylindrical shape, and has a diameter that is not smaller than the outside diameter of the thread on the lower portion.

9 Claims, 6 Drawing Figures

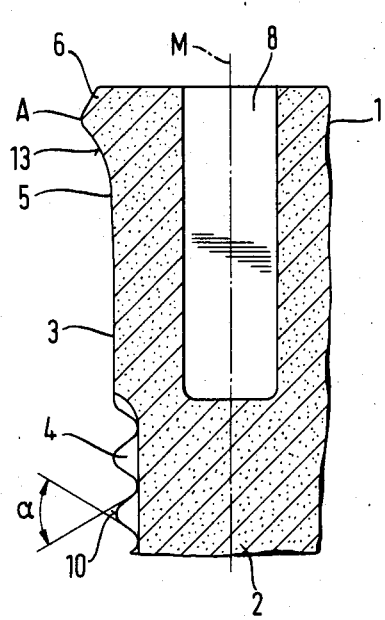
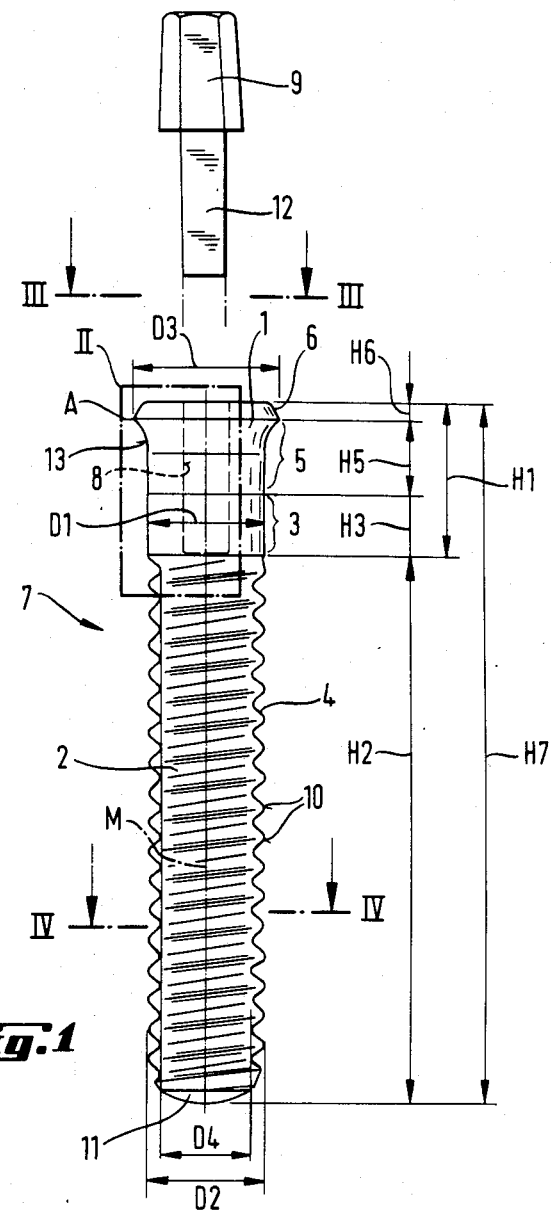
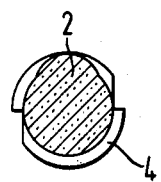
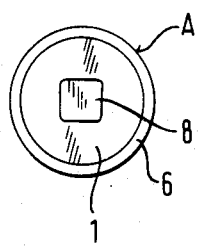

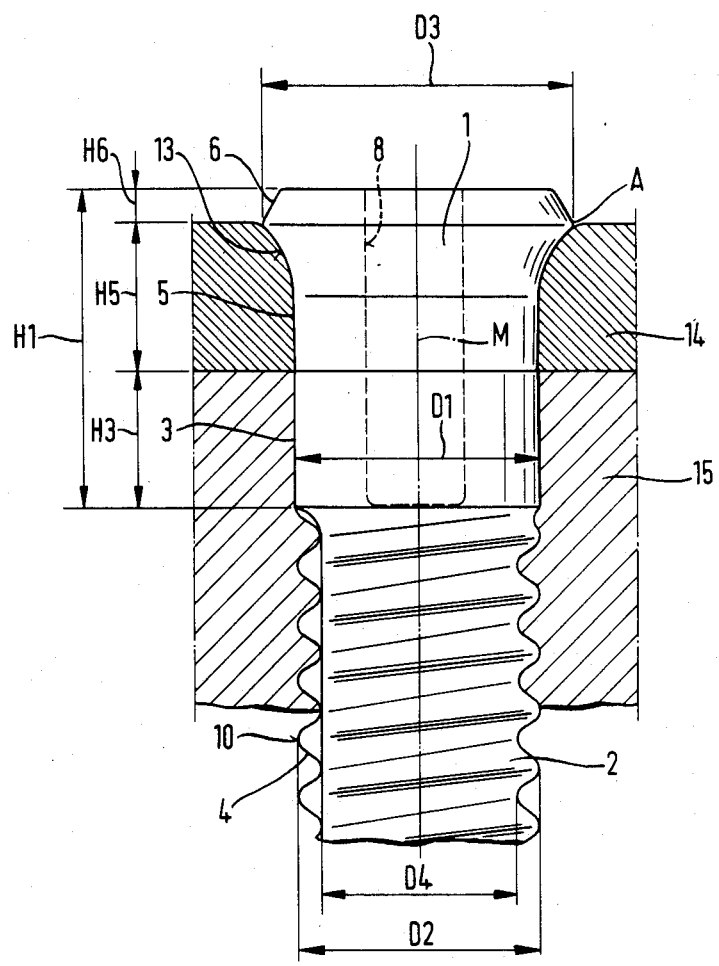

JAW IMPLANT FOR RECEIVING A REPLACEMENT-TOOTH HOLDER

The present invention relates to jaw implants of the type with a lower portion having a screw thread and with a screw head, which has an upper portion with an opening to receive a replacement-tooth holder.

Screw-like jaw implants are known. German publication OS No. 25 40 077 describes one-piece cylindrical screw bodies with a hexagonally configured screw head for fastening an artificial tooth by means of cement. Its disadvantage is that the stresses developed by chewing shortly cause a loosening of the implant and pockets leading to focal infections develop in the area of tne screw head. To counter these disadvantages, German OS No. 25 40 077 proposes the fixation of the cylindrical screw body with a truncopyramidal top nut which is screwed onto the upper threads of the screw body which project from the upper side of the jawbone and whose bottom surface engages the jawbone. Disadvantages of this proposal are not only the complex implantation technique, but also the danger that, due to the atrophy of the bone, the implant may develop the character of a hybrid, i.e., a combination of intraosseous and subperiosteal rooting of one and the same implant body. In such an implant, niches and tunneling develop on the subperiosteal portion with the disadvantage of heightened danger of infection. The disadvantage of the proposal to provide an additional nut on the end of the screw body in some cases to improve fixation resides in the fact that a bore to match the diameter of the nut must be provided, which will result in a larger void around the cylindrical screw body, which in the course of the healing-in process fills up slowly with spongy tissue so that during the healing-in phase the cylindrical screw body does not contribute to the fixation of the implant. If only one top nut is used, disadvantages arise due to the fact that only a very small portion is situated in the cortical bone tissue and by far the greatest portion is in the gingival tissue where it can contribute very little to the fixation of the implant. Another disadvantage is that the top nut protruding from the gingival tissue into the oral cavity is an obstacle to instinctive tongue movements, so that the healing-in process cannot take place undisturbed, because slight shifts of the inserted implant take place which greatly interfere with the healing process.

German publication OS No. 26 15 116 relates to a further development of the proposal described above and provides for placing one or more flanges underneath the top nut. In some cases the use of a top nut can be dispensed with, so that the fixation of the implant is performed exclusively by the cylindrical screw and the flange or flanges. These proposals too have the above-described disadvantages of a complex implantation technique, consisting of the drilling of a hole having different-size diameters and a very specific depth, and it is especially striking that a relatively large incision has to be made for the installation of the flange or flanges in the gingival tissue, which is filled to only a slight extent by the screw head provided for receiving the artificial tooth or by the top nut, so that a relatively slow healing of the incision is to be expected. In addition, there remain the disadvantages of the so-called "hybrid implant" mentioned in connection with German OS No. 25 40 077, and the disadvantage that the tongue encounters the screw head protruding from the crest of the jawbone.

The screw-like implant body described in German OS No. 26 28 443 also has the disadvantage that its screw head protrudes into the oral cavity. The self-tapping screw threads, which are partially interrupted at certain intervals so that new bone tissue can form preferentially in these interruptions, are disadvantageous to the extent that at first they are not filled with bone tissue and do not contribute to primary stability. The decided disadvantage, however, is that, in the area of the hexagonally configured screw head, which serves for engagement by a screwdriving tool and has a smaller diameter than the outside diameter of the threads, voids are formed in the area of the cortical bone tissue, which are at least not immediately filled by bone tissue after implantation. Even assuming that both the end of the screw and the threads situated directly under the screw head extend into the harder cortical bone tissue, the danger exists, due to the configuration of the threads as self-tapping, that concentrations of pressure occur at the crests of the threads which result in severe stress on the bone tissue and in some cases can produce premature loosening of the implant.

More recent proposals, as disclosed in German OS No. 30 43 336 and German Pat. No. 32 41 963, provide head pieces to accommodate the superstructure or an artificial tooth, which are not placed until after the implant has healed in, so that the above-described danger of the loosening of the implant by tongue movements during the implant healing phase is largely avoided.

In the implant disclosed in German OS No. 30 43 336, due to the section of low conical configuration underneath the sleeve provided for embedding at the gingivae, the disadvantage exists of a small area of contact with the cortical bone tissue, so that in this especially important area of the jaw a still inadequate fixation is to be expected, especially in the case of cortical bone tissue that is not flat. Also disadvantageous is the fact that at the top no closure by bone tissue or connective tissue is achieved that would securely fix the implant. Furthermore, the conical saw-tooth thread illustrated therein causes concentrations of pressure at the thread crests when chewing pressure is applied, which result in severe stressing of the bone tissue and in some cases lead to the loosening of the implant. According to German Pat. No. 32 41 963, therefore, in the case of a conically shaped, screw-like implant, an annular bead and annular constrictions are provided between the upper part and the conical screw part, the diameter of the bead being smaller than the diameter of the thread crests in the topmost thread of the conical threaded part. Although in this case the so-called tunneling is largely avoided, the disadvantage still exists that a certain void remains in the area of the annular bead or annular constrictions, which only gradually refills with bone tissue, so that this area of the implant can contribute little to the firm seating of the implant during the healing phase.

German OS No. 33 15 329 provides a cylindrical jaw implant having a cutting thread in its middle portion. The disadvantage of this implant is that the cylindrical portion situated above the cutting thread has the same diameter as the core diameter in the threaded portion, so that above the threads a void is formed which corresponds to the depth of the threads. Thus, in the case of transverse stress, the implant is exposed in this upper area to a certain tilting moment. Also disadvantageous is the complex form of the implant, which greatly adds to the difficulty of manufacture from hard-to-work materials, such as ceramic.

The present invention aims to make available a jaw implant which will have a simple construction and consequently will call for an uncomplicated implantation procedure. In particular, the invention makes available a jaw implant which is capable, due to its external form, of preventing better than has been possible heretofore the development of dead voids in the bone immediately after its placement in the jawbone, so as thus to produce an enlarged support zone, especially in the area of the cortical bone tissue, by which the implant will receive a secure seating from the very outset.

For the insertion of the jaw implant of the invention, a hole is drilled in the jawbone to match the core diameter of the thread on the entire length of the implant. The female thread is cut in this bore all the way to the bottom with a threading tap. After the insertion of a guiding pin, a countersink mills the seat for the cylindrical portion of the screw head. The implant is screwed into the hole such that the cylindrical part of the screw head completely fills out the counterbore. The cylindrical shape of the screw head assures that no harmful voids or pockets will form in the cortical bone area. The cylindrical configuration of the screw head also prevents the occurrence of pressure concentrations in the cortical area as a result of chewing stresses, such as those which are observed especially in the sawtooth-like thread disclosed in German OS No. 30 43 336. In the cortical area the implant has an especially large bearing surface and even during the healing-in phase it receives an especially secure seating.

The bottom part in the form of a cylindrical screw leads to the additional advantage that the bottom portion can easily be cut to the required length without the need to have on hand a number of implants of different length. Another advantage of a cylindrical bottom part is that, immediately after insertion, the threads, by being rounded, will have an optimum seating in the bore provided with the precut threads.

The truncoconical configuration in the upper portion, which has an opening to accommodate a replacement-tooth holder, serves for the achievement of a tight closure and compensates for a possibly not perfectly flat seating at the surface of the upper portion.

In accordance with the invention, a jaw implant having a longitudinal axis comprises a lower supporting portion and an implant head having a cylindrical portion lying adjacent to the lower portion and having a coronal-end, truncoconical portion with an opening for the accomodation of a replacement-tooth holder. The lower portion has the form of a cylindrical screw having a supporting thread thereon. The implant includes a portion adjoining the coronal-end portion in the apical direction and having an external contour which is in one region convexly curved and then runs parallel with the longitudinal axis of the implant so that the adjoining portion merges transitionlessly with the cylindrical portion of the implant head. The coronal-end portion has a greater cross-sectional area at one end thereof and the adjoining portion has a greater cross-sectional area at one end thereof lying against the greater cross-sectional area of the coronal-end portion. The diameter of the cylindrical portion is not smaller than the outside diameter of the supporting thread, the supporting thread merging directly with the cylindrical portion. The adjoining portion and the cylindrical portion each have an opening communicating with the opening of the cylindrical portion, for the accomodation of a replacement-tooth holder.

For a better understanding of the invention, together with other and further objects thereof, reference is made to the following description, taken in connection with the accompanying drawings, and its scope will be pointed out in the appended claims.

Referring now to the drawings:

FIG. 1 is a side elevational diagrammatic view of a jaw implant constructed in accordance with the invention, together with a replacement-tooth holder shown in the uninstalled state;

FIG. 2 is an enlarged fragmentary view of the implant in the region II of FIG. 1;

FIG. 3 is a top view of the implant taken from the line III—III of FIG. 1;

FIG. 4 is a section of the implant taken along line IV—IV of FIG. 1;

FIG. 5 shows the jaw implant of FIG. 1 inserted into a jawbone;

FIG. 1 shows a jaw implant 7 preferably of aluminum oxide, in accordance with the invention. The jaw implant preferably has a total length H7 of 23 mm. The cylindrical bottom portion 2 is slightly rounded at its extremity 11 and preferably has a length H2 of 18 mm. Thread 4 is formed on the cylindrical bottom portion 2, which thread preferably has a flank angle alpha equal to 60 degrees (FIG. 2). The bottom portion 2 merges with the cylindrically shaped portion 3 of the screw head 1. The screw head 1 preferably has a length H1 totaling at least 3.2 mm and the bottom portion 2 merges with the portion 5 and the latter with the upper portion 6. The length H1 preferably amounts to no more than 50% of the total length H7 of the jaw implant. The portion 5 preferably is of approximately truncoconical shape and the portion 6 preferably is of truncoconical shape, the portion 6 preferably having a height H6 of 0.5 mm, amounting to between 7 and 15% of the height H1 of the screw head 1. At point A, where portions 5 and 6 merge with one another, they have a common cross-sectional area forming the major base of the two truncated approximately conical portions, preferably with a diameter D3 of 5 mm. In the upper portion 6 and in the portions 5 and 3, an opening 8 is provided for the accommodation of a shank 12 of the replacement-tooth holder 9. The screw head 1 preferably has a height H1 of 4 to 8 mm. The diameter D1 in the cylindrical portion 3 amounts to 4 mm and preferably corresponds to the outside diameter D2 of the thread 4. The core diameter D4 preferably is 3.1 mm. The diameter D1 is not smaller than the outside diameter D2 of the thread 4. The diameter D3 preferably is 20 to 30% greater than the diameter D1, D2. The diameter D1 of the portion 3 is up to 75% greater than the diameter D2 of the bottom portion 2. The outside diameter D2 of the thread 4 preferably is 20 to 30% greater than the core diameter D4 of the bottom portion 2. The thread 4 has a flank angle alpha preferably of 58 to 62 degrees. The edges 10 of the thread 4 preferably are rounded with a radius r=0.16 to 0.2 mm. The jaw implant preferably comprises high-purity aluminum oxide.

As shown in FIG. 2, the external contours 13 of portion 5 below the merging point preferably are convex, i.e., they curve inwardly toward the central axis M of the jaw implant 7. The thread 4 preferably has a rounding 10 with a radius r=0.18 mm. FIG. 3 shows that the opening 8 preferably has a square cross section with rounded corners.

In FIG. 5 is shown the seating of the jaw implant 7 of the invention with screw head 1 and upper thread 4 in the gingivae 14 and in the cortical bone tissue 15, respectively. It can be seen that a considerable part of the cylindrical portion 3, namely, height H3, for example, of at least 1.5 mm, and preferably of 2 to 5 mm, is tightly engaged with the cortical bone tissue 15, while portion 5 is surrounded by gingival tissue 14. The cortical tissue 15 is also intimately engaged with the thread 4 of the bottom portion 2 which is represented only partially.

While there have been described what are at present considered to be the preferred embodiments of this invention, it will be obvious to those skilled in the art that various changes and modifications may be made therein without departing from the invention, and it is, therefore, aimed to cover all such changes and modifications as fall within the true spirit and scope of the invention.

What is claimed is:

1. A jaw implant having a longitudinal axis, comprising:
    a lower supporting portion;
    an implant head having a cylindrical portion lying adjacent said lower portion and having a coronal-end, truncoconical portion with an opening for the accommodation of a replacement-tooth holder;
    said lower portion having the form of a cylindrical screw having a supporting thread thereon;
    a portion adjoining said coronal-end portion in the apical direction and having an external contour which first tapers toward said longitudinal axis of the implant and is then configured parallel to said longitudinal axis of the implant so that said adjoining portion merges transitionlessly with said cylindrical portion of said implant head, said coronal-end portion having a greater cross-sectional area at one end thereof and said adjoining portion having a greater cross-sectional area at one end thereof lying against said greater cross-sectional area of said coronal-end portion;
    the height of said coronal-end, truncoconical portion amounting to between 7 and 15% of the height of said implant head;
    the diameter of said cylindrical portion being not smaller than the outside diameter of said supporting thread, said supporting thread merging directly with said cylindrical portion;
    the edges of said thread being rounded with a radius $r = 0.16$ to $0.2$ mm;
    said adjoining portion and said cylindrical portion each having an opening communicating with said opening of said coronal-end portion, for the accommodation of a replacement-tooth holder.

2. A jaw implant in accordance with claim 1, in which said cylindrical portion has a height of 4 to 8 mm.

3. A jaw implant in accordance with claim 1, in which the implant head has a height of 2 to 5 mm for tight engagement with cortical bone tissue.

4. A jaw implant in accordance with claim 1, in which the height of the screw head amounts to no more than 50% of the total height of the jaw implant.

5. A jaw implant in accordance with claim 1, in which the diameter of said greater cross-sectional area of said coronal-end portion is 20 to 30% greater than the diameter of said cylindrical portion of said screw head.

6. A jaw implant in accordance with claim 1, in which the diameter of said cylindrical portion of said screw head is up to 75% greater than the outside diameter of the thread of the bottom portion.

7. A jaw implant in accordance with claim 1, in which the outside diameter of the thread is 20 to 30% greater than the core diameter of the bottom portion.

8. A jaw implant in accordance with claim 1, in which the thread has a flank angle alpha of 58 to 62 degrees.

9. A jaw implant in accordance with claim 1, in which the jaw implant consists of high-purity aluminum oxide.

* * * * *